(12) United States Patent
Williamson et al.

(10) Patent No.: US 10,933,074 B2
(45) Date of Patent: Mar. 2, 2021

(54) METHODS FOR IMPROVING THE GASTROINTESTINAL TOLERANCE OF FOOD AND BEVERAGE PRODUCTS COMPRISING SWEET, LOW-DIGESTIBLE CARBOHYDRATES

(71) Applicant: Tate & Lyle Ingredients Americas LLC, Hoffman Estates, IL (US)

(72) Inventors: Patricia S. Williamson, Hoffman Estates, IL (US); Ryan D. Woodyer, Hoffman Estates, IL (US)

(73) Assignee: Tate & Lyle Ingredients Americas LLC, Hoffman Estates, IL (US)

( * ) Notice: Subject to any disclaimer, the term of this patent is extended or adjusted under 35 U.S.C. 154(b) by 0 days.

(21) Appl. No.: 15/762,304

(22) PCT Filed: Sep. 21, 2016

(86) PCT No.: PCT/GB2016/052932
§ 371 (c)(1),
(2) Date: Mar. 22, 2018

(87) PCT Pub. No.: WO2017/051166
PCT Pub. Date: Mar. 30, 2017

(65) Prior Publication Data
US 2018/0264018 A1 Sep. 20, 2018

Related U.S. Application Data

(60) Provisional application No. 62/222,478, filed on Sep. 23, 2015.

(30) Foreign Application Priority Data

Feb. 10, 2016 (GB) .................................... 1602410

(51) Int. Cl.
| | | |
|---|---|---|
| *A61K 31/7004* | (2006.01) | |
| *A61K 31/716* | (2006.01) | |
| *A23L 2/60* | (2006.01) | |
| *A23L 33/17* | (2016.01) | |
| *A23L 33/125* | (2016.01) | |
| *A23L 33/21* | (2016.01) | |
| *A61K 31/7016* | (2006.01) | |
| *A23L 27/30* | (2016.01) | |
| *A23L 2/52* | (2006.01) | |
| *A61K 31/721* | (2006.01) | |

(Continued)

(52) U.S. Cl.
CPC .......... *A61K 31/7004* (2013.01); *A23L 2/52* (2013.01); *A23L 2/60* (2013.01); *A23L 2/66* (2013.01); *A23L 27/30* (2016.08); *A23L 27/31* (2016.08); *A23L 27/33* (2016.08); *A23L 27/34* (2016.08); *A23L 27/35* (2016.08); *A23L 27/38* (2016.08); *A23L 33/10* (2016.08); *A23L 33/125* (2016.08); *A23L 33/17* (2016.08); *A23L 33/21* (2016.08); *A23L 33/26* (2016.08); *A61K 31/7016* (2013.01); *A61K 31/716* (2013.01); *A61K 31/721* (2013.01); *A23V 2002/00* (2013.01); *A23V 2200/32* (2013.01)

(58) Field of Classification Search
CPC .......... A23L 33/10; A23L 33/17; A23L 27/38; A23L 27/35; A23L 27/34; A23L 27/31; A23L 27/30; A23L 33/125; A23L 33/26; A23L 2/66; A23L 27/33; A23L 33/21; A23L 2/52; A23L 2/60; A61K 31/716; A61K 31/721; A61K 31/7004; A61K 31/7016; A61K 2300/00; A23V 2002/00; A23V 2200/32; A23V 2250/384; A23V 2250/5108; A23V 2250/5116; A23V 2250/54; A23V 2250/55; A23V 2250/61; A23V 2200/00; A23V 2250/00; A23V 2200/30; A23V 2250/602; A23V 2250/606; A23V 2250/612; A23V 2250/64; A23V 2250/6402; A23V 2250/6401; A23V 2250/6412; A23V 2250/6416; A23V 2250/642; A23V 2250/6422

See application file for complete search history.

(56) References Cited

U.S. PATENT DOCUMENTS 3,766,165 A * 10/1973 Rennhard ............ A23C 9/1544
536/123.1
3,876,794 A * 4/1975 Rennhard ................ A23G 1/56
426/548

(Continued)

FOREIGN PATENT DOCUMENTS

| CN | 1510992 A | 7/2004 |
| CN | 102475180 A | 5/2012 |

(Continued)

OTHER PUBLICATIONS

Grabitske et al., "Gastrointestinal Effects of Low-Digestible Carbohydrates", Critical Reviews in Food Science and Nutrition, 2009, vol. 49, pp. 327-360.

(Continued)

*Primary Examiner* — Lawrence E Crane
(74) *Attorney, Agent, or Firm* — RatnerPrestia

(57) ABSTRACT

The present invention relates to methods for improving the gastrointestinal tolerance of food and beverage products comprising sweet, low-digestible carbohydrates, and the use of one or more of D-glucose, fiber and protein for improving the gastrointestinal tolerance of food and beverage products comprising sweet, low-digestible carbohydrates.

25 Claims, 6 Drawing Sheets

(51) Int. Cl.
*A23L 33/10* (2016.01)
*A23L 33/26* (2016.01)
*A23L 2/66* (2006.01)

(56) References Cited

U.S. PATENT DOCUMENTS

| | | | |
|---|---|---|---|
| 4,042,714 A * | 8/1977 | Torres | A21D 2/18 |
| | | | 426/62 |
| 4,134,999 A | 1/1979 | Muhler et al. | |
| 4,304,768 A * | 12/1981 | Staub | A23L 33/22 |
| | | | 426/558 |
| 4,379,782 A | 4/1983 | Staub et al. | |
| 4,962,094 A | 10/1990 | Jamas et al. | |
| 5,028,437 A | 7/1991 | Jerrett | |
| 6,399,142 B1 * | 6/2002 | Silver | C08B 37/0054 |
| | | | 426/548 |
| 7,147,883 B1 | 12/2006 | Silver | |
| 7,186,431 B1 * | 3/2007 | Silver | A23L 29/244 |
| | | | 426/548 |
| 8,071,558 B2 | 12/2011 | Tokuda et al. | |
| 8,735,108 B2 | 5/2014 | Hong et al. | |
| 9,049,876 B2 * | 6/2015 | Fujihara | A23L 2/60 |
| 9,109,266 B2 * | 8/2015 | Takamine | A23L 2/60 |
| 9,717,267 B2 * | 8/2017 | Prakash | A23L 2/60 |
| 2006/0051480 A1 | 3/2006 | Miles | |
| 2006/0286248 A1 | 12/2006 | Anfinsen et al. | |
| 2010/0112174 A1 | 5/2010 | Christensen et al. | |
| 2010/0130435 A1 | 5/2010 | Tokuda et al. | |
| 2010/0204346 A1 | 8/2010 | Okuma et al. | |
| 2011/0081476 A1 | 4/2011 | Lee et al. | |
| 2012/0070534 A1 | 3/2012 | Suzuki | |
| 2012/0076908 A1 | 3/2012 | Fujihara et al. | |
| 2012/0094940 A1 | 4/2012 | Takamine et al. | |
| 2013/0274350 A1 | 10/2013 | Okuma et al. | |
| 2013/0323362 A1 | 12/2013 | Penhasi | |
| 2014/0322389 A1 | 10/2014 | Prakash et al. | |
| 2014/0342044 A1 | 11/2014 | Bell et al. | |
| 2015/0110940 A1 | 4/2015 | Lee et al. | |
| 2015/0216199 A1 | 8/2015 | Porter et al. | |
| 2016/0151305 A1 | 6/2016 | Takako et al. | |

FOREIGN PATENT DOCUMENTS

| | | | |
|---|---|---|---|
| CN | 102919964 A | | 2/2013 |
| CN | 102972676 A | | 3/2013 |
| JP | 61500433 A | | 3/1986 |
| JP | 2010018528 | | 1/2010 |
| WO | 2008082596 A2 | | 7/2008 |
| WO | 2014007606 A1 | | 1/2014 |
| WO | 2014175119 A1 | | 10/2014 |
| WO | 2015075473 A | | 5/2015 |
| WO | 2015094342 A1 | | 6/2015 |

OTHER PUBLICATIONS

Hishiike et al., "Transepithelial Transports of Rare Sugar D-Psicose in Human Intestine", Journal of Agricultural and Food Chemistry, 2013, vol. 61, pp. 7381-7386.

Iida et al., "Estimation of Maximum Non-effect Level of D-Psicose in Causing Diarrhea in Human Subjects" with English Abstract, Journal of Japanese Council for Advanced Food Ingredients Research, 2007, vol. 10, No. 1, pp. 15-19.

International Search Report and Written Opinion for International Application No. PCT/GB2016/052932, dated Feb. 8, 2017, 30 pages.

Knudsen, K.E., "Lactose in Diet Influences the Degradation of Mixed Linked β(1-3;1-4)-D-glucan in the Small Intestine of Pigs", J. Anim. Sci. 2012, vol. 90, pp. 125-127.

Great Britain Combined Search Report and Examination for Application No. GB1602410.1, dated Jul. 19, 2016, 7 pages.

Third Party Observation for International Application No. PCT/GB2016/052932, dated Jul. 20, 2017, 4 pages.

International Preliminary Report on Patentability for International Application No. PCT/GB2016/052932, dated Mar. 27, 2018, 23 pages.

European Communication for European Application No. 16 775 821.8, dated Jan. 10, 2020, 7 pages.

Kneepkens et al., "Incomplete Intestinal Absorption of Fructose", Archives of Disease in Childhood, 1984, vol. 59, pp. 735-738.

Iida et al, "Estimation of Maximum Non-Effect Level of D-Psicose in Causing Diarrhea in Human Subjects" with partial Journal of Japanese Council for Advanced Food Ingredients Research, 2007, vol. 10, No. 1, pp. 15-19.

English Translation of Japanese Office Action for Japanese Application No. 2018-534032, dated Jun. 16, 2020, 8 pages.

Chinese Office Action for Chinese Application No. 201680055582.0, dated Oct. 30, 2020 with translation, 34 pages.

Beaugerie et al., "Sorbitol Absorption in the Healthy Human Small Intestine is Increased by the Concomitant Ingestion of Glucose or Lipids", Eur J Gastroenterol Hespatol., 1995, vol. 7, No. 2, pp. 125-128 (abstract only).

Hoekstra et al., "Facilitating Effect of Amino Acids on Fructose and Sorbitol Absorption in Children", J Pediatr Gastroenterol Nutr., 1996, vol. 23, No. 2, pp. 118-124 (Abstract only).

Iga et al., "Effect of d-Allose on Glycemic Responses After Oral Carbohydrate Tolerance in Rats", Technical Bulletin of Faculty of Faculty of Agriculture—Kagawa University, 2009 (2 pgs.) (abstract only).

Japanese Third Party Observations for Japanese Applications No. 2018-534032, dated Oct. 14, 2028 with translation, 8 pages.

\* cited by examiner

METHODS FOR IMPROVING THE GASTROINTESTINAL TOLERANCE OF FOOD AND BEVERAGE PRODUCTS COMPRISING SWEET, LOW-DIGESTIBLE CARBOHYDRATES

CROSS-REFERENCE TO RELATED APPLICATIONS

This is the national phase of International Application No. PCT/GB2016/052932, filed 21 Sep. 2016, which claims priority to United Kingdom Application No. 1602410.1, filed 10 Feb. 2016 and U.S. Provisional Application No. 62/222,478, filed 23 Sep. 2015. The disclosure of each of these applications is incorporated herein by reference in its entirety for all purposes.

FIELD OF THE INVENTION

The present invention relates to methods for improving the gastrointestinal tolerance of food and beverage products comprising sweet, low-digestible carbohydrates, and the use of one or more of D-glucose, fiber and protein for improving the gastrointestinal tolerance of food and beverage products comprising sweet, low-digestible carbohydrates.

BACKGROUND OF THE INVENTION

Public health agencies and expert scientific organizations are encouraging the food industry to reduce calorie content and portion sizes in an effort to prevent and decrease obesity. Low- and no-calorie sweeteners that reduce calorie content in foods while meeting taste expectations are anticipated to help to meet these goals.

Displacement of calories with low and no-calorie sweetener alternatives such as sweet, low-digestible carbohydrates is considered to help with weight maintenance through reduced energy intake. However, one potential problem with the use of sugar substitutes and sweeteners is that some consumers can exhibit gastrointestinal sensitivities to the ingredients used to displace calories, such as the commonly used sweet, low-digestible carbohydrates erythritol, mannitol, and sorbitol (Grabitske, H. A.; Slavin, J. L.; Crit. Rev. Food. Sci. Nutr., 2009, 49, 327-360).

Absorption of carbohydrates from the intestinal tract is important to digestive comfort. Consumption of sugars, and sugar substitutes is often clinically evaluated to identify their gastric tolerance limits. The gastrointestinal intolerances of dietary carbohydrates and sweeteners are noted by consumers as the commonly experienced symptoms of gas, bloating, distension, and diarrhea. For example, in healthy adults, if more than 45 g of carbohydrates reaches the colon at any one time, it can cause osmotic diarrhea. Carbohydrate malabsorption can thus produce an acceleration of colonic transit and fluid overload of the colon.

Dietary increases in sweet, low-digestible carbohydrates (e.g. sugar alcohols), which are less well absorbed, can lead to increased amounts of carbohydrate material going into the colon.

In view of the above, there is a need for new ways to improve the gastrointestinal tolerance of food and beverage products comprising carbohydrates, in particular, sweet, low-digestible carbohydrates, in high levels, so as to make it possible to have higher inclusion rates in foods without resulting symptoms.

It has surprisingly been found that D-glucose, fiber (e.g. dietary fiber), in particular, beta-glucan and polydextrose, and protein can improve the gastrointestinal tolerance of food and beverage products comprising a sweet, low-digestible carbohydrate.

SUMMARY OF THE INVENTION

The present invention relates to methods for improving the gastrointestinal tolerance of food and beverage products comprising a sweet, low-digestible carbohydrate, and to the use of one or more of D-glucose, fiber and protein in these methods.

According to an aspect of the present invention, there is provided a method for improving the gastrointestinal tolerance of a food or beverage product comprising a sweet, low-digestible carbohydrate, wherein the method comprises incorporating one or more of D-glucose, fiber and protein into the food or beverage product.

In some embodiments of the present invention, the fiber is dietary fiber. In certain embodiments of the present invention, the fiber is one or more of beta-glucan and polydextrose.

In an embodiment, the method comprises incorporating D-glucose into the food or beverage product. In another embodiment, the method comprises incorporating fiber into the food or beverage product. In a further embodiment, the method comprises incorporating protein into the food or beverage product.

In an embodiment, the method comprises incorporating beta-glucan into the food or beverage product. In an alternative embodiment, the method comprises incorporating polydextrose into the food or beverage product. In further embodiments, the method comprises incorporating beta-glucan and polydextrose into the food or beverage product.

In certain embodiments, the method comprises incorporating D-glucose and fiber into the food or beverage product. For example, the method comprises incorporating D-glucose and beta-glucan into the food or beverage product. In another example, the method comprises incorporating D-glucose and polydextrose into the food or beverage product. In a further embodiment, the method comprises incorporating D-glucose, beta-glucan and polydextrose into the food or beverage product.

In further embodiments, the method comprises incorporating D-glucose and protein into the food or beverage product. In other further embodiments, the method comprises incorporating fiber and protein into the food or beverage product. For example, the method comprises incorporating protein and beta-glucan into the food or beverage product. In another example, the method comprises incorporating protein and polydextrose into the food or beverage product. In a further example, the method comprises incorporating protein, beta-glucan and polydextrose into the food or beverage product.

In another embodiment, the method comprises incorporating D-glucose, fiber and protein into the food or beverage product. For example, the method comprises incorporating D-glucose, beta-glucan and protein into the food or beverage product. In another example, the method comprises incorporating D-glucose, polydextrose and protein into the food or beverage product. In a further example, the method comprises incorporating D-glucose, beta-glucan, polydextrose and protein into the food or beverage product.

The sweet, low-digestible carbohydrate may be selected from the group consisting of lactose, sugar alcohols and rare sugars. Preferred sweet, low-digestible carbohydrates include sorbitol, maltitol, isomalt, isomaltulose, erythritol, D-and L-xylitol, D- and L-allose, D-and L-tagatose, lactose, melezitose, D- and L-arabinose, L-fructose, L-glucose and D- and L-allulose. Further preferred low-digestible carbohydrates include D-sorbitol, lactose, erythritol, D-xylitol, D-tagatose, L-allulose, maltitol and isomaltulose.

In embodiments of the present invention wherein the method comprises incorporating at least D-glucose into the food or beverage product, the sweet, low-digestible carbohydrate is preferably present in the food or beverage product in a weight ratio to D-glucose of from about 0.5:1 to about 10:1, for example, in a weight ratio to D-glucose of from about 1:1 to about 5:1 or in a weight ratio to D-glucose of from about 1:1 to about 3:1. More preferably, the sweet, low-digestible carbohydrate is present in the food or beverage product in a weight ratio to D-glucose of about 1:1.

In embodiments of the present invention wherein the method comprises incorporating at least beta-glucan into the food or beverage product, the beta-glucan is preferably present in an amount of about 0.5 g to about 6 g per labeled serving of the food or beverage product.

In other embodiments of the present invention wherein the method comprises incorporating at least beta-glucan into the food or beverage product, the beta-glucan is present in an amount of about 0.01% by weight to about 20% by weight with respect to the total weight of the food or beverage product.

According to some embodiments of the invention, the beta-glucan is oat beta-glucan.

Preferably, the beta-glucan is present in the food or beverage product in the form of a fraction rich in soluble dietary fibers containing at least about 20% and up to about 40% beta-glucan (on a dry weight basis) of mean molecular weight of at least about 800 kDa. More preferably, the beta-glucan is in the form of a fraction rich in soluble dietary fibers containing about 35% beta-glucan (on a dry weight basis) of mean molecular weight of at least about 800 kDa.

In embodiments of the present invention wherein the method comprises incorporating at least polydextrose into the food or beverage product, the polydextrose is present in an amount of about 0.1 g to about 40 g per labeled serving of the food or beverage product.

In other embodiments of the present invention wherein the method comprises incorporating at least polydextrose into the food or beverage product, the polydextrose is preferably present in an amount of about 0.1% by weight to about 80% by weight (e.g. about 0.5% by weight to about 50% by weight) with respect to the total weight of the food or beverage product.

In embodiments of the present invention wherein the method comprises incorporating at least protein into the food or beverage product, the protein is present in an amount of about 0.1 g to about 40 g per labeled serving of the food or beverage product.

In other embodiments of the present invention wherein the method comprises incorporating at least protein into the food or beverage product, the protein is present in an amount of about 0.1% by weight to about 80% by weight with respect to the total weight of the food or beverage product.

According to some embodiments of the present invention, the sweet, low-digestible carbohydrate is present in the food or beverage product in a total amount from about 1 g to about 100 g (e.g. from about 1 g to about 25 g) per labeled serving.

According to another aspect of the present invention, there is provided the use of one or more of D-glucose, fiber and protein in a method for improving the gastrointestinal tolerance of a food or beverage product comprising a sweet, low-digestible carbohydrate, wherein the method comprises incorporating one or more of D-glucose, fiber and protein into the food or beverage product.

According to another aspect of the present invention, there is provided the use of a composition comprising one or more of D-glucose, fiber and protein in a method for improving the gastrointestinal tolerance of a food or beverage product comprising a sweet, low-digestible carbohydrate, wherein the method comprises incorporating one or more of D-glucose, fiber and protein into the food or beverage product.

According to another aspect of the present invention, there is provided the use of D-glucose for increasing the gastrointestinal tolerance of a food or beverage product comprising a sweet, low-digestible carbohydrate.

According to another aspect of the present invention, there is provided the use of fiber for increasing the gastrointestinal tolerance of a food or beverage product comprising a sweet, low-digestible carbohydrate.

In an embodiment, there is provided the use of beta-glucan for increasing the gastrointestinal tolerance of a food or beverage product comprising a sweet, low-digestible carbohydrate.

In another embodiment, there is provided the use of polydextrose for increasing the gastrointestinal tolerance of a food or beverage product comprising a sweet, low-digestible carbohydrate.

In a further embodiment, there is provided the use of a combination of polydextrose and beta-glucan for increasing the gastrointestinal tolerance of a food or beverage product comprising a sweet, low-digestible carbohydrate.

According to another aspect of the present invention, there is provided the use of protein for increasing the gastrointestinal tolerance of a food or beverage product comprising a sweet, low-digestible carbohydrate.

According to another aspect, there is provided the use of a combination of D-glucose and fiber for increasing the gastrointestinal tolerance of a food or beverage product comprising a sweet, low-digestible carbohydrate.

In an embodiment, there is provided the use of a combination of D-glucose and polydextrose for increasing the gastrointestinal tolerance of a food or beverage product comprising a sweet, low-digestible carbohydrate.

In another embodiment, there is provided the use of a combination of D-glucose and beta-glucan for increasing the gastrointestinal tolerance of a food or beverage product comprising a sweet, low-digestible carbohydrate.

In a further embodiment, there is provided the use of a combination of D-glucose, beta-glucan and polydextrose for increasing the gastrointestinal tolerance of a food or beverage product comprising a sweet, low-digestible carbohydrate.

According to another aspect, there is provided the use of a combination of D-glucose and protein for increasing the gastrointestinal tolerance of a food or beverage product comprising a sweet, low-digestible carbohydrate.

According to another aspect, there is provided the use of a combination of fiber and protein for increasing the gastrointestinal tolerance of a food or beverage product comprising a sweet, low-digestible carbohydrate.

In an embodiment, there is provided the use of a combination of protein and polydextrose for increasing the gastrointestinal tolerance of a food or beverage product comprising a sweet, low-digestible carbohydrate.

In another embodiment, there is provided the use of a combination of protein and beta-glucan for increasing the gastrointestinal tolerance of a food or beverage product comprising a sweet, low-digestible carbohydrate.

In a further embodiment, there is provided the use of a combination of protein, beta-glucan and polydextrose for increasing the gastrointestinal tolerance of a food or beverage product comprising a sweet, low-digestible carbohydrate.

According to another aspect, there is provided the use of a combination of D-glucose, fiber and protein for increasing the gastrointestinal tolerance of a food or beverage product comprising a sweet, low-digestible carbohydrate.

In an embodiment, there is provided the use of a combination of D-glucose, polydextrose and protein for increasing the gastrointestinal tolerance of a food or beverage product comprising a sweet, low-digestible carbohydrate.

In another embodiment, there is provided the use of a combination of D-glucose, beta-glucan and protein for increasing the gastrointestinal tolerance of a food or beverage product comprising a sweet, low-digestible carbohydrate.

In a further embodiment, there is provided the use of a combination of D-glucose, beta-glucan, polydextrose and protein for increasing the gastrointestinal tolerance of a food or beverage product comprising a sweet, low-digestible carbohydrate.

According to a further aspect, there is provided one or more of D-glucose, fiber and protein, or a composition comprising one or more of D-glucose, fiber and protein, for use in a method for improving the gastrointestinal tolerance of food and beverage products comprising a sweet, low-digestible carbohydrate in accordance with earlier aspects of the invention.

According to another aspect of the present invention, there is provided a food or beverage product comprising a sweet, low-digestible carbohydrate and one or more of D-glucose, fiber and protein, wherein the one or more of D-glucose, fiber and protein are present in an amount effective to improve the gastrointestinal tolerance of said food or beverage product.

DETAILED DESCRIPTION

Figure 1:
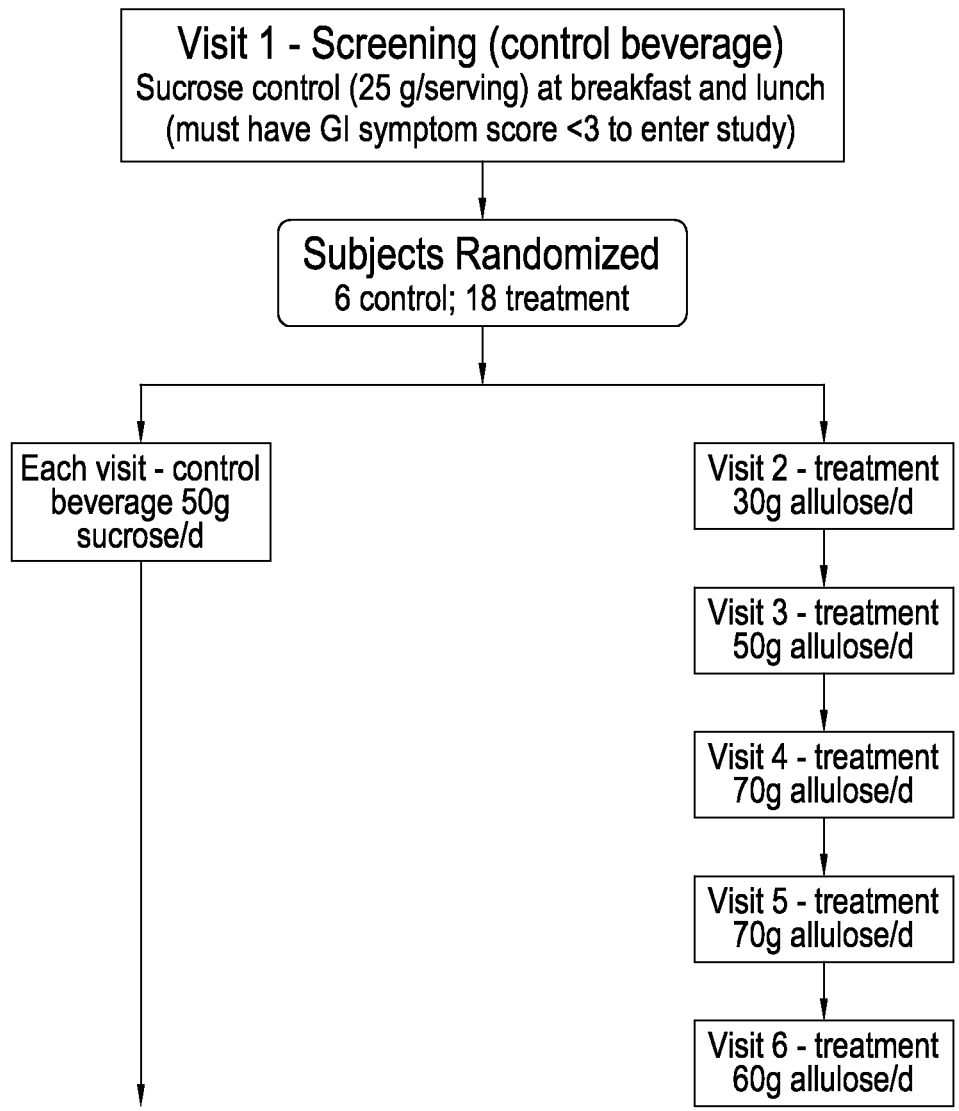
FIG. 1 is a schematic of the treatment protocol used in Example 1.

Displacement of calories with low and no-calorie alternatives could help with weight maintenance through reduced energy intake, but as these low and no-calorie ingredients are used at increasing levels in the food supply there is concern about the gastrointestinal tolerance of the ingredients. Accordingly, the present invention is particularly concerned with methods for improving the gastrointestinal tolerance of food and beverage products comprising sweet, low-digestible carbohydrates.

The present invention is based on the surprising finding that one or more of D-glucose, fiber (wherein the fiber is preferably one or more of beta-glucan and polydextrose) and protein can improve the gastrointestinal tolerance of food and beverage products comprising sweet, low-digestible carbohydrates.

According to an aspect of the present invention, there is provided a method for improving the gastrointestinal tolerance of a food or beverage product comprising a sweet, low-digestible carbohydrate, wherein the method comprises incorporating one or more of D-glucose, fiber (wherein the fiber is preferably one or more of beta-glucan and polydextrose) and protein into the food or beverage product.

In certain embodiments, the method comprises incorporating only one of D-glucose, fiber and protein into the food or beverage product. For example, the method may comprise incorporating D-glucose, fiber or protein into the food or beverage product.

In other embodiments, the method comprises incorporating only one of D-glucose, beta-glucan and polydextrose into the food or beverage product. For example, the method may comprise incorporating D-glucose, beta-glucan or polydextrose into the food or beverage product.

In other embodiments, the method comprises incorporating D-glucose and fiber into the food or beverage product.

In further embodiments, the method comprises incorporating any two of D-glucose, beta-glucan and polydextrose into the food or beverage product. For example, the method may comprise incorporating a combination of: D-glucose and beta-glucan; D-glucose and polydextrose; or beta-glucan and polydextrose into the food or beverage product.

In another embodiment, the method comprises incorporating D-glucose, beta-glucan and polydextrose into the food or beverage product. In other words, the method may comprise incorporating a combination of D-glucose, beta-glucan and polydextrose into the food or beverage product.

In further embodiments, the method comprises incorporating D-glucose and protein into the food or beverage product. In other further embodiments, the method comprises incorporating fiber and protein into the food or beverage product. For example, the method may comprise incorporating protein and beta-glucan into the food or beverage product. In another example, the method comprises incorporating protein and polydextrose into the food or beverage product. In a further example, the method comprises incorporating protein, beta-glucan and polydextrose into the food or beverage product.

In a further embodiment, the method comprises incorporating D-glucose, fiber and protein into the food or beverage product. For example, the method may comprise incorporating D-glucose, beta-glucan and protein into the food or beverage product. In another example, the method comprises incorporating D-glucose, polydextrose and protein into the food or beverage product. In a further example, the method comprises incorporating D-glucose, beta-glucan, polydextrose and protein into the food or beverage product.

Sweet, low-digestible carbohydrates are carbohydrates that are sweet to taste, and when consumed at high levels (e.g. more than 20-30 g/day), have been known to cause gastrointestinal responses such as abdominal distension, abdominal pains, borborygmus, increased flatus, loose stools, and nausea/vomiting when consumed as part of a food or beverage product, particularly in sensitive individuals. Sweet, low-digestible carbohydrates include lactose, sugar alcohols and rare sugars.

In the context of the present invention, the term "sweet to taste" means that the sweet, low-digestible carbohydrates are at least 20% as sweet as sucrose, but less than five times as sweet as sucrose on an equal weight basis according to a paired comparison test. In order to determine that a low-digestible carbohydrate has less than 5 times the sweetness of sucrose, the assessment involves making solutions in neutral pH water of sucrose at 15% by weight and the test solution at 3% by weight and performing sweetness paired comparison testing. If the test solution at 3% by weight is sweeter than sucrose at 15% by weight then the test sweetener is greater than 5 times the sweetness of sucrose. In order to determine that a low-digestible carbohydrate has at least 20% of the sweetness of sucrose, the assessment involves making solutions in neutral pH water of test sweetener at 15% by weight and the sucrose solution at 3% by weight and performing sweetness paired comparison. If the test solution at 15% by weight is sweeter than sucrose at 3% by weight then the test sweetener is at least 20% the sweetness of sucrose.

In the context of the present invention, the term "fiber" refers to one or more carbohydrates having a degree of polymerization greater than 3 that resist digestion in the intestine. In certain embodiments, the fiber is dietary fiber. Fibers which may be contemplated in the present invention include cellulose, hemicellulose (e.g. xylan, glucuronoxylan, arabinoxylan, glucomannan and xyloglucan), inulin, lignin, beta-glucan, pectin, polydextrose, psyllium, resistant starch and wheat dextrin. In preferred embodiments, the fiber is one or more of beta-glucan and polydextrose.

Sugar alcohols are also known as polyols. Examples of sugar alcohols include sorbitol, maltitol, isomalt, erythritol, xylitol, lactitol, and mannitol. Sugar alcohols are generally able to provide a degree of calorie reduction (by way of example, sorbitol provides about 2.6 kcal/g compared to about 4 kcal/g for sucrose). However, these sweeteners are often not suitable for use at high levels due to low gastrointestinal tolerance.

Rare sugars are monosaccharides which occur in very small quantities in nature. They include, but are not limited to L-sugars, D-allose, D-allulose, D-tagatose, D-turanose, D-leucrose, lactulose, trehalose and isomaltulose. Excessive consumption of rare sugars can lead to gastrointestinal issues.

Certain individuals lack the ability to digest lactose as a result of having insufficient levels of lactase, which is an enzyme that catalyzes the hydrolysis of lactose into glucose and galactose. If undigested, lactose will travel into the gut where it acts as food for gas-producing gut flora. Therefore, consumption of lactose by intolerant individuals, or excessive consumption of lactose by individuals that are able to produce normal levels of lactase, can cause gastrointestinal issues.

Symptoms associated with the gastrointestinal intolerance of sugar alcohols, rare sugars and lactose include, but are not limited to, abdominal distension, abdominal pains, borborygmus, increased flatus, loose stools, and nausea/vomiting. Accordingly, in the context of the present invention, improving the gastrointestinal tolerance of a food or beverage product comprising a sweet, low-digestible carbohydrate involves reducing the occurrence and severity of the some or all of the symptoms associated with gastrointestinal intolerance following ingestion of a food or beverage product comprising a sweet, low-digestible carbohydrate. The methods of the present invention may also improve the gastrointestinal tolerance to the extent that there is an absence of the symptoms of sweet, low-digestible carbohydrate consumption.

According to certain embodiments of the present invention, the sweet, low-digestible carbohydrate is one or more selected from the group consisting of sorbitol, maltitol, isomalt, isomaltulose, erythritol, xylitol, D- and L-allose, D-and L-tagatose, lactose, melezitose, D- and L-arabinose, L-fructose, L-glucose and D- and L-allulose. In preferred embodiments, the low-digestible carbohydrate is one or more selected from the group consisting of D-sorbitol, lactose, maltitol, erythritol, D-xylitol, D-tagatose, L-allulose, maltitol and isomaltulose.

Food or beverage products which may be contemplated in the context of the present invention include baked goods; sweet bakery products (including, but not limited to, rolls, cakes, pies, pastries, and cookies); pre-made sweet bakery mixes for preparing sweet bakery products; pie fillings and other sweet fillings (including, but not limited to, fruit pie fillings and nut pie fillings such as pecan pie filling, as well as fillings for cookies, cakes, pastries, confectionary products and the like, such as fat-based cream fillings); desserts, gelatins and puddings; frozen desserts (including, but not limited to, frozen dairy desserts such as ice cream—including regular ice cream, soft serve ice cream and all other types of ice cream—and frozen non-dairy desserts such as non-dairy ice cream, sorbet and the like); carbonated beverages (including, but not limited to, soft (i.e. non-alcoholic) carbonated beverages); non-carbonated beverages (including, but not limited to, soft non-carbonated beverages such as flavored waters and sweet tea or coffee based beverages); beverage concentrates (including, but not limited to, liquid concentrates and syrups as well as non-liquid 'concentrates', such as freeze-dried and/or powder preparations); yogurts (including, but not limited to, full fat, reduced fat and fat-free dairy yogurts, as well non-dairy and lactose-free yogurts and frozen equivalents of all of these); snack bars (including, but not limited to, cereal, nut, seed and/or fruit bars); bread products (including, but not limited to, leavened and unleavened breads, yeasted and unyeasted breads such as soda breads, breads comprising any type of wheat flour, breads comprising any type of non-wheat flour (such as potato, rice and rye flours), gluten-free breads); pre-made bread mixes for preparing bread products; sauces, syrups and dressings; sweet spreads (including, but not limited to, jellies, jams, butters, nut spreads and other spreadable preserves, conserves and the like); confectionary products (including, but not limited to, jelly candies, soft candies, hard candies, chocolates and gums); sweetened breakfast cereals (including, but not limited to, extruded (kix type) breakfast cereals, flaked breakfast cereals and puffed breakfast cereals); and cereal coating compositions for use in preparing sweetened breakfast cereals. Other types of food or beverage product not mentioned here but which conventionally include one or more low- or non-digestible carbohydrate may also be contemplated in the context of the present invention.

The sweet, low-digestible carbohydrate in the food or beverage products may be present in an amount of up to about 80% by weight relative to the total weight of the food or beverage product, for example, in an amount of from about 1% by weight to about 80% by weight relative to the total weight of the food or beverage product. All intermediate amounts (i.e. 2%, 3%, 4% . . . 77%, 78%, 79% by weight relative to the total weight of the food or beverage product) are contemplated, as are all intermediate ranges based on these amounts.

According to certain embodiments of the present invention, the sweet, low-digestible carbohydrate is present in the food or beverage product in an amount from about 1 g to about 100 g per labeled serving (or portion) of the food or beverage product. All intermediate amounts (i.e. 2 g, 3 g, 4 g . . . 97 g, 98 g, 99 g) are contemplated, as are all intermediate ranges based on these amounts. For example, the low-digestible carbohydrate may be present in an amount from about 5 g to about 90 g, about 5 g to about 80 g, about 10 g to about 80 g, about 10 g to about 70 g, about 15 g to about 70 g, about 15 g to about 60 g, or about 15 g to about 50 g per labeled serving of the food or beverage product.

The labeled serving refers to the manufacturer's suggested portion size of a particular food or beverage that an individual should consume in any one sitting. The suggested portion size will vary depending on the type of food or beverage product. For example, a food product may have a suggested portion size of between about 10 g to about 300 g, whereas a beverage product may have a suggested portion size of between about 25 ml to about 500 ml. Accordingly, the labeled serving for a food product may be between about 10 g to about 300 g and the labeled serving for a beverage product may be between about 25 ml to about 500 ml.

When the food or beverage product is a carbonated beverage, the carbonated beverage may comprise the sweet, low digestible carbohydrate in an amount of from about 2% by weight to about 25% by weight relative to the total weight of the carbonated beverage, for example in an amount of from about 2% by weight to about 20% by weight relative to the total weight of the carbonated beverage, for example in an amount of from about 2% by weight to about 15% by weight relative to the total weight of the carbonated beverage, for example in an amount of from about 2% by weight to about 7% by weight relative to the total weight of the carbonated beverage, for example in an amount of from about 4% by weight to about 6% by weight relative to the total weight of the carbonated beverage, for example in an amount of about 2%, 2.2%, 3%, 4%, 4.5%, 5%, 5.5%, 6%, 6.5%, 7%, 8%, 9%, 10%, 15%, 20% or 25% by weight relative to the total weight of the carbonated beverage.

When the food or beverage product is a non-carbonated beverage, the non-carbonated beverage may comprise the sweet, low digestible carbohydrate in an amount of from about 1% by weight to about 25% by weight relative to the total weight of the non-carbonated beverage, for example in an amount of from about 2% by weight to about 20% by weight relative to the total weight of the non-carbonated beverage, for example in an amount of from about 2% by weight to about 15% by weight relative to the total weight of the non-carbonated beverage, for example in an amount of from about 2% by weight to about 7% by weight relative to the total weight of the non-carbonated beverage, for example in an amount of from about 4% by weight to about 6% by weight relative to the total weight of the non-carbonated beverage, for example in an amount of about 1%, 1.5%, 2%, 2.5%, 3%, 3.5%, 4%, 4.5%, 5%, 5.5% 6%, 6.5%, 7%, 8%, 9%, 10%, 15%, 20% or 25% by weight relative to the total weight of the non-carbonated beverage.

In certain embodiments, the food or beverage product does not contain any other sweeteners other than the sweet, low digestible carbohydrate and the D-glucose (if present) used to improve the gastrointestinal tolerance of the food or beverage product comprising the sweet, low digestible carbohydrate. However, in other embodiments, it may be desirable to include another sweetener or sweeteners. Thus, the food or beverage product may contain one or more natural or artificial co-sweetener.

Various natural high intensity sweeteners may be used as the one or more co-sweetener. Specific examples include monk fruit extracts and stevia extracts, as well as any sweet compounds isolated from such extracts (including synthetic equivalents of such compounds).

Monk fruit is the fruit of the *siraitia grosvenorii* vine, also known as luo han guo. The sweet taste of monk fruit extracts is mainly attributed to a family of compounds known as 'mogrosides', examples of which include mogroside V, mogroside IV, mogroside VI, oxomogroside V, mogroside IIIE, neomogroside and siamenoside I. Monk fruit extracts, as well as sweeteners comprising any one or more mogroside, may be used as the one or more co-sweetener. Extracts or sweeteners comprising mogroside V are particularly preferred.

*Stevia*, or *Stevia rebaudiana*, contains sweet compounds in its leaves. These compounds may be extracted to provide stevia extracts. The sweet taste of stevia extracts is mainly attributed to a family of compounds known as 'steviol glycosides', examples of which include rebaudiosides (i.e., rebaudioside A to F, M, N and X), rubusoside, stevioside, and dulcosides. Stevia extracts, as well as sweeteners comprising any one or more steviol glycoside, may be used as the one or more co-sweetener. Extracts or sweeteners comprising rebaudioside A (Reb A) are particularly preferred. Blends or mixtures of individual steviol glycosides which have been individually isolated, produced and/or purified may also be used to advantage.

The stevia extract for use as the one or more co-sweetener preferably comprises steviol glycosides in a total amount of at least 90 weight %, preferably in a total amount of 95 weight % or more, relative to the total weight of the stevia extract on a dry solids basis. For example, the stevia extract may comprise steviol glycosides in a total amount of at least 90, 91, 92, 93, 94, 95, 96, 97, 98 or 99 weight %, relative to the total weight of the stevia extract on a dry solids basis.

A preferred stevia extract for use as the one or more co-sweetener comprises Rebaudioside A and Stevioside in a combined total amount of at least 70 weight %, preferably in a combined total amount of 75 weight % or more, relative to the total weight of the stevia extract on a dry solids basis. Another preferred stevia extract for use as the one or more co-sweetener comprises Rebaudioside B in an amount of from about 15 weight % to about 30 weight %, preferably from about 19 weight % to about 23 weight %, relative to the combined total weight of steviol glycosides in the stevia extract on a dry solids basis.

One circumstance where it may be desirable or necessary to include one or more co-sweetener is where regulatory restrictions prescribe a maximum amount of the sweet, low-digestible carbohydrate to be used in a particular type of food or beverage product. An example of such regulatory restrictions is the GRAS (Generally Recognized as Safe) regime prescribed by the Food and Drug Administration (FDA) in the United States. Where regulatory restrictions of this type apply, the sweet, low-digestible carbohydrate may be used up to its maximum allowable usage amount, and one or more co-sweetener may be used to provide any additional sweetness required.

One aspect of the present invention relates to the unexpected finding that D-glucose can improve the gastrointestinal tolerance of a food or beverage product comprising a sweet, low-digestible carbohydrate. Specifically, this aspect provides a method for improving the gastrointestinal tolerance of a food or beverage product comprising a sweet, low-digestible carbohydrate, wherein the method comprises incorporating D-glucose into the food or beverage product.

In embodiments of the present invention wherein the method comprises incorporating only D-glucose into the food or beverage product (i.e. fiber and protein are not incorporated into the food or beverage product) the at least one carbohydrate is preferably selected from the group consisting of D-and L-tagatose, erythritol, D- and L-allulose.

In embodiments of the present invention wherein the method comprises incorporating D-glucose into the food or beverage product, the sweet, low-digestible carbohydrate may be present in the food or beverage product in a weight ratio to D-glucose of from about 0.5:1 to about 10:1 (for example, about 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, 5:1, 5.1:1, 5.2:1, 5.3:1, 5.4:1, 5.5:1, 5.6:1, 5.7:1, 5.8:1, 5.9:1, 6:1, 6.1:1, 6.2:1, 6.3:1, 6.4:1, 6.5:1, 6.6:1, 6.7:1, 6.8:1, 6.9:1, 7:1, 7.1:1, 7.2:1, 7.3:1, 7.4:1, 7.5:1, 7.6:1, 7.7:1, 7.8:1, 7.9:1, 8:1, 8.1:1, 8.2:1, 8.3:1, 8.4:1, 8.5:1, 8.6:1, 8.7:1, 8.8:1, 8.9:1, 9:1, 9.1:1, 9.2:1, 9.3:1, 9.4:1, 9.5:1, 9.6:1, 9.7:1, 9.8:1, 9.9:1 and 10:1). In an embodiment, the sweet, low-digestible carbohydrate is present in the food or beverage product in a weight ratio to D-glucose of from about 1:1 to about 5:1. Preferably, the sweet, low-digestible carbohydrate is present in the food or beverage product in a weight ratio to D-glucose of from about 1:1 to about 4:1, more preferably in a weight ratio to D-glucose of from about 1:1 to about 3:1. Even more preferably, the sweet, low-digestible carbohydrate is present in the food or beverage product in a weight ratio to D-glucose of about 1:1.

In certain embodiments of the present invention, the sweet, low-digestible carbohydrate is D-allulose and the method comprises incorporating D-glucose into the food or beverage product, wherein the D-allulose is present in the food or beverage product in a weight ratio to D-glucose of from about 1:1 to about 4:1. Preferably, the D-allulose is present in a weight ratio to D-glucose of from about 1:1 to about 3:1. In a more preferred embodiment, the D-allulose is present in a weight ratio to D-glucose of about 1:1.

The food or beverage product may comprise the sweet, low-digestible carbohydrate in an amount between about 10 g and about 50 g per labeled serving, and D-glucose in an amount between about 10 g and about 50 g per labeled serving. All intermediate amounts (i.e. 11 g, 12 g, 13 g . . . 47 g, 48 g, 49 g per labeled serving) are contemplated, as are all intermediate ranges based on these amounts. In certain embodiments, the food or beverage product comprises the sweet, low-digestible carbohydrate in an amount between about 20 g and about 50 g per labeled serving (for example, about 25 g, 35 g, or 45 g per labeled serving) and D-glucose in an amount between about 20 g and about 50 g per labeled serving (for example, about 25 g, 35 g, or 45 g per labeled serving).

In certain embodiments, the food or beverage comprises D-allulose in an amount between about 20 g and about 50 g per labeled serving, and D-glucose in an amount between about 20 g and about 50 g per labeled serving. In an embodiment, the food or beverage comprises D-allulose in an amount of about 25 g per labeled serving, and D-glucose in an amount of about 25 g per labeled serving. In another embodiment, the food or beverage comprises D-allulose in an amount of about 35 g per labeled serving, and D-glucose in an amount of about 35 g per labeled serving. In another embodiment, the food or beverage comprises D-allulose in an amount of about 45 g per labeled serving, and D-glucose in an amount of about 45 g per labeled serving.

Another aspect of the present invention relates to the unexpected finding that fiber (in particular, beta-glucan and polydextrose) can improve the gastrointestinal tolerance of a food or beverage product comprising a sweet, low-digestible carbohydrate.

In embodiments of the present invention wherein the method comprises incorporating fiber into the food or beverage product, the fiber is preferably present in an amount of about 0.1 g to about 50 g per labeled serving of the food or beverage product. All intermediate amounts (i.e. 1 g, 2 g, 3 g . . . 47 g, 48 g, 49 g per labeled serving) are contemplated, as are all intermediate ranges based on these amounts.

In other embodiments of the present invention wherein the method comprises incorporating at least fiber into the food or beverage product, the fiber is present in an amount of about 0.1% by weight to about 80% by weight with respect to the total weight of the food or beverage product. All intermediate amounts (i.e. 1%, 2%, 3% . . . 77%, 78%, 79% by weight relative to the total weight of the food or beverage product) are contemplated, as are all intermediate ranges based on these amounts.

When the method comprises incorporating at least fiber into the food or beverage product, the sweet, low-digestible carbohydrate may be present in the food or beverage product in a weight ratio to fiber of from about 100:1 to about 5:1 (for example, about 95:1, 90:1, 85:1, 80:1, 75:1, 70:1, 65:1, 60:1, 55:1, 50:1, 45:1, 40:1, 35:1, 30:1, 25:1, 20:1, 15:1, 10:1 and 5:1). In an embodiment, the sweet, low-digestible carbohydrate is present in the food or beverage product in a weight ratio to fiber of from about 50:1 to about 5:1. Preferably, the sweet, low-digestible carbohydrate is present in the food or beverage product in a weight ratio to fiber of from about 50:1 to about 10:1, more preferably in a weight ratio to fiber of from about 40:1 to about 10:1. Even more preferably, the sweet, low-digestible carbohydrate is present in the food or beverage product in a weight ratio to fiber of from about 30:1 to about 20:1 (e.g. 25:1).

In certain embodiments, the food or beverage comprises D-allulose in an amount between about 10 g and about 50 g per labeled serving, and fiber in an amount between about 0.5 g and about 6.0 g per labeled serving. In an embodiment, the food or beverage comprises D-allulose in an amount between about 10 g and about 40 g per labeled serving, and fiber in an amount between about 0.5 g and about 4.0 g per labeled serving. In another embodiment, the food or beverage comprises D-allulose in an amount between about 20 g and about 40 g per labeled serving, and fiber in an amount between about 0.5 g and about 2.0 g per labeled serving. In another embodiment, the food or beverage comprises D-allulose in an amount between about 20 g and about 30 g per labeled serving, and fiber in an amount between about 0.5 g and about 1.5 g per labeled serving. In another embodiment, the food or beverage comprises D-allulose in an amount of about 25 g per labeled serving, and fiber in an amount of about 1.0 g per labeled serving.

In a preferred embodiment of this aspect, there is provided a method for improving the gastrointestinal tolerance of a food or beverage product comprising a sweet, low-digestible carbohydrate, wherein the method comprises incorporating beta-glucan into the food or beverage product. In other words, the fiber is beta-glucan.

Beta-glucans are soluble dietary fibers from oat and barley grains. Beta-glucans can be obtained from other natural sources such as yeast and mushrooms. In structural terms, beta-glucans are mixed-linkage (1-3), (1-4) β-D-glucose polymers. The mean molecular weight of beta-glucan has been reported to vary between 50 and 3000 kDa. In the present invention, the mean molecular weight of the beta-glucan is between about 1 and about 10000 kDa. Preferably, the mean molecular weight of the beta-glucan is between about 100 and about 1000 kDa In preferred embodiments of the present invention, the beta-glucan is oat beta-glucan.

In other preferred embodiments, the beta-glucan is present in the food or beverage product in the form of a fraction rich in soluble dietary fibers containing at least about 20% and up to about 40% beta-glucan (on a dry weight basis) of mean molecular weight of at least about 800 kDa. More preferably, the beta-glucan is present in the food or beverage product in the form of a fraction rich in soluble dietary fibers containing about 35% beta-glucan (on a dry weight basis) of mean molecular weight of at least about 800 kDa Beta-glucans are capable of making viscous, shear thinning solutions, even at low concentrations. The viscosity of beta-glucans is dependent on their concentration in aqueous solution. In the present invention, the beta-glucan may have low, medium or high viscosity. For example, the beta-glucan may be a beta-glucan that has a specific viscosity in the range of about 1 cSt to about 20 cSt when at a concentration of 0.5% by weight in water (relative to the total weight of the aqueous solution). Alternatively, the beta-glucan may have a specific viscosity in the range of about 20 cSt to about 50 cSt when at a concentration of 0.5% by weight (e.g. about 20 cSt to about 30 cSt when at a concentration of 0.5% by weight). In other embodiments, the beta-glucan may have a specific viscosity that is greater than about 50 cSt when at a concentration of 0.5% by weight (e.g. greater than about 100 cSt when at a concentration of 0.5% by weight).

In embodiments of the present invention wherein the method comprises incorporating beta-glucan into the food or beverage product, the beta-glucan is preferably present in an amount between about 0.5 g and about 6 g (for example, about 1 g, 2 g, 3 g, 4 g, 5 g, or 6 g) per labeled serving of the food or beverage product. In embodiments of the invention where the beta-glucan is in the form of a fraction rich in soluble dietary fibers containing about 35% beta-glucan (on a dry weight basis) of mean molecular weight of at least about 800 kDa, the beta-glucan is preferably present in an amount of about 1.5 g per labeled serving of the food or beverage product.

Alternatively, the beta-glucan is incorporated in the food or beverage product in an amount of between about 0.01% by weight to about 20% by weight with respect to the total weight of the food or beverage product. All intermediate amounts (i.e. 1%, 2%, 3% . . . 17%, 18%, 19% by weight relative to the total weight of the food or beverage product) are contemplated, as are all intermediate ranges based on these amounts. For example, beta-glucan may be incorporated in the food or beverage product in an amount of between about 0.1% by weight to about 20% by weight, between about 0.5% by weight to about 20% by weight, between about 0.5% by weight to about 10% by weight, between about 0.5% by weight to about 5% by weight (e.g. between about 0.5% by weight to about 3% by weight, or between about 0.75% by weight to about 2% by weight), between about 0.1% by weight to about 10% by weight, or between about 0.1% by weight to about 5% by weight (e.g. between about 0.1% by weight to about 3% by weight, or between about 0.1% by weight to about 2% by weight).

Further, when the method comprises incorporating beta-glucan into the food or beverage product, the sweet, low-digestible carbohydrate may be present in the food or beverage product in a weight ratio to beta-glucan of from about 100:1 to about 5:1 (for example, about 95:1, 90:1, 85:1, 80:1, 75:1, 70:1, 65:1, 60:1, 55:1, 50:1, 45:1, 40:1, 35:1, 30:1, 25:1, 20:1, 15:1, 10:1 and 5:1). In an embodiment, the sweet, low-digestible carbohydrate is present in the food or beverage product in a weight ratio to beta-glucan of from about 50:1 to about 5:1. Preferably, the sweet, low-digestible carbohydrate is present in the food or beverage product in a weight ratio to beta-glucan of from about 50:1 to about 10:1, more preferably in a weight ratio to beta-glucan of from about 40:1 to about 10:1. Even more preferably, the sweet, low-digestible carbohydrate is present in the food or beverage product in a weight ratio to beta-glucan of from about 30:1 to about 20:1 (e.g. 25:1).

In certain embodiments, the food or beverage comprises D-allulose in an amount between about 10 g and about 50 g per labeled serving, and beta-glucan in an amount between about 0.5 g and about 6.0 g per labeled serving. In an embodiment, the food or beverage comprises D-allulose in an amount between about 10 g and about 40 g per labeled serving, and beta-glucan in an amount between about 0.5 g and about 4.0 g per labeled serving. In another embodiment, the food or beverage comprises D-allulose in an amount between about 20 g and about 40 g per labeled serving, and beta-glucan in an amount between about 0.5 g and about 2.0 g per labeled serving. In another embodiment, the food or beverage comprises D-allulose in an amount between about 20 g and about 30 g per labeled serving, and beta-glucan in an amount between about 0.5 g and about 1.5 g per labeled serving. In another embodiment, the food or beverage comprises D-allulose in an amount of about 25 g per labeled serving, and beta-glucan in an amount of about 1.0 g per labeled serving.

In embodiments of the present invention wherein the method comprises incorporating only beta-glucan into the food or beverage product (i.e. D-glucose, other fibers and protein are not incorporated into the food or beverage product) the sweet, low-digestible carbohydrate is one or more selected from the group consisting of sorbitol, maltitol, isomalt, isomaltulose, erythritol, xylitol, D- and L-allose, D-and L-tagatose, lactose, melezitose, D- and L-arabinose, L-fructose, L-glucose and D- and L-allulose.

In another preferred embodiment of this aspect, there is provided a method for increasing the gastrointestinal tolerance of a food or beverage product comprising a sweet, low-digestible carbohydrate, wherein the method comprises incorporating polydextrose into the food or beverage product. In other words, the fiber is polydextrose.

Polydextrose is a synthetic polymer of glucose. More specifically, it is a randomly bonded condensation polymer of D-glucose (in which 1,6-glycosidic linkages predominate), sorbitol (in an amount up to 10% by weight) and one of citric acid or phosphoric acid (in amounts up to 1% by weight). Polydextrose may also contain small amounts of free D-glucose, sorbitol, citric acid and 1,6-anhydro-D-glucose (levoglucosan). The polydextrose may have a molecular weight in the range of 162 g/mol to 20000 g/mol. In certain embodiments, 90% or more of the polydextrose molecules have a molecular weight between about 504 g/mol and about 5000 g/mol. In some embodiments, the average degree of polymerisation of the polydextrose is 12.

In embodiments of the invention, the average molecular weight of the polydextrose is approximately 2000 g/mol.

In embodiments of the present invention wherein the method comprises incorporating polydextrose into the food or beverage product, the polydextrose is preferably present in an amount between about 0.1 g and about 40 g per labeled serving of the food or beverage product. All intermediate amounts (i.e. 1 g, 2 g, 3 g . . . 37 g, 38 g, 39 g per labeled serving) are contemplated, as are all intermediate ranges based on these amounts.

Alternatively, the polydextrose is incorporated in the food or beverage product in an amount of between about 0.1% by weight to about 80% by weight with respect to the total weight of the food or beverage product. All intermediate amounts (i.e. 1%, 2%, 3% . . . 77%, 78%, 79% by weight relative to the total weight of the food or beverage product) are contemplated, as are all intermediate ranges based on these amounts. For example, the polydextrose may incorporated in the food or beverage product in an amount of between about 0.1% by weight to about 70% by weight, between about 0.5% by weight to about 70% by weight (e.g. between about 0.5% by weight to about 50% by weight), between about 1% by weight to about 70% by weight, between about 10% by weight to about 70% by weight, between about 20% by weight to about 70% by weight, between about 30% by weight to about 70% by weight or between about 40% by weight to about 70% by weight (e.g. between about 55% by weight to about 65%, by weight, or between about 45% by weight to about 55% by weight).

In embodiments of the present invention wherein the method comprises incorporating only polydextrose into the food or beverage product (i.e. D-glucose, other fibers and protein are not incorporated into the food or beverage product) the sweet, non-digestible carbohydrate is selected from one or more of sorbitol, maltitol, isomalt, isomaltulose, erythritol, xylitol, D- and L-allose, D-and L-tagatose, lactose, melezitose, D- and L-arabinose, L-fructose, L-glucose and D- and L-allulose.

Another aspect of the present invention relates to the unexpected finding that protein can improve the gastrointestinal tolerance of a food or beverage product comprising a sweet, low-digestible carbohydrate.

In embodiments of the present invention wherein the method comprises incorporating protein into the food or beverage product, the protein is present in an amount of about 0.1 g to about 40 g per labeled serving of the food or beverage product.

In other embodiments, the protein is present in an amount of about 0.1% by weight to about 80% by weight with respect to the total weight of the food or beverage product.

The method according to this aspect may further comprise incorporating one or more of D-glucose and fiber into the food or beverage product.

The protein may be native or non-native. A native protein is a protein that has not been altered by denaturing agents. In contrast, a non-native protein is a protein that has undergone chemical and/or enzymatic treatment. For example, the protein may be hydrolyzed protein, which is a protein that has been hydrolyzed into its component amino acids.

In an embodiment of the invention, the protein may be one or more of vegetable protein (e.g. corn, wheat, barley, spelt, rye and oat) and milk protein. An example of a protein derived from oat is one available from Tate & Lyle under the trade name PrOatein™.

In embodiments of the present invention wherein the method comprises incorporating only protein into the food or beverage product (i.e. D-glucose and fiber are not incorporated into the food or beverage product) the sweet, non-digestible carbohydrate is selected from one or more of sorbitol, maltitol, isomalt, isomaltulose, erythritol, xylitol, D- and L-allose, D-and L-tagatose, lactose, melezitose, D- and L-arabinose, L-fructose, L-glucose and D- and L-allulose.

The one or more of D-glucose, fiber (e.g. beta-glucan and polydextrose) and protein may be provided in a syrup ingredient or dry ingredient mix, which can be incorporated within food or beverage products.

The one or more of D-glucose, fiber (e.g. beta-glucan and polydextrose) and protein may be incorporated into the food or beverage product during the manufacturing process. Alternatively, the one or more of D-glucose, fiber (e.g. beta-glucan and polydextrose) and protein may be incorporated into the food or beverage product following the manufacture of said food or beverage product. The one or more of D-glucose, fiber (e.g. beta-glucan and polydextrose) and protein may also be incorporated immediately prior to consumption of the food or beverage product.

In other embodiments of the present invention, the sweet, low-digestible carbohydrate may be provided with one or more of D-glucose, fiber (e.g. beta-glucan and polydextrose) and protein in a syrup ingredient or dry ingredient mix, which can be incorporated within food or beverage products, for example, during or following manufacture, or immediately prior to consumption of said food or beverage products.

When cooking at home, home cooks will often be following a recipe which calls for sugar (i.e. sucrose, or table sugar). Sweet, low-digestible carbohydrates represent an alternative to sugar in many food and beverage applications.

From a practical point of view, it is convenient for a home cook to be able to replace the sugar in any given recipe with the sweet, low-digestible carbohydrate without having to calculate how much sweet, low-digestible carbohydrate is required. Thus, the sweet, low-digestible carbohydrate and one or more of D-glucose, fiber (e.g. beta-glucan or polydextrose) and protein may be incorporated as part of a scoop-for-scoop sweetener, which can be used to replace sucrose on an equivalent volume basis (i.e. one scoop of the mix comprising the sweet, low-digestible carbohydrate and one or more of D-glucose, fiber (e.g. beta-glucan or polydextrose) and protein is used to replace one scoop of sugar).

In addition to scoop-for-scoop products, there is also demand among end users for table-top sweeteners that can be used in place of sugar or other nutritive sweeteners. In the case of table-top products, there is no need for the sweetness to be equivalent to that of sucrose on a volume basis; instead, table-top sweeteners are simply supplied with dosage guidelines, often with reference to a teaspoon (5 mL) of sugar. The most common use for table-top products is to sweeten beverages, typically hot beverage products such as tea and coffee. The sweet, low-digestible carbohydrate and one or more of D-glucose, fiber (e.g. beta-glucan or polydextrose) and protein may therefore be provided as a table-top sweetener.

According to another aspect of the present invention, there is provided the use of one or more of D-glucose, fiber and protein in a method for improving the gastrointestinal tolerance of a food or beverage product comprising a sweet, low-digestible carbohydrate, wherein the method comprises incorporating one or more of D-glucose, fiber and protein into the food or beverage product.

In an embodiment, there is provided the use of D-glucose in a method for improving the gastrointestinal tolerance of a food or beverage product comprising a sweet, low-digestible carbohydrate, wherein the method comprises incorporating D-glucose into the food or beverage product.

In an embodiment, there is provided the use of fiber in a method for improving the gastrointestinal tolerance of a food or beverage product comprising a sweet, low-digestible carbohydrate, wherein the method comprises incorporating fiber into the food or beverage product. In a preferred embodiment, there is provided the use of beta-glucan and/or polydextrose in a method for improving the gastrointestinal tolerance of a food or beverage product comprising a sweet, low-digestible carbohydrate, wherein the method comprises incorporating one or more of beta-glucan and/or polydextrose into the food or beverage product.

In an embodiment, there is provided the use of protein in a method for improving the gastrointestinal tolerance of a food or beverage product comprising a sweet, low-digestible carbohydrate, wherein the method comprises incorporating protein into the food or beverage product.

In an embodiment, there is provided the use of D-glucose and fiber in a method for improving the gastrointestinal tolerance of a food or beverage product comprising a sweet, low-digestible carbohydrate, wherein the method comprises incorporating D-glucose and fiber into the food or beverage product. In a preferred embodiment, there is provided the use of D-glucose and beta-glucan and/or polydextrose in a method for improving the gastrointestinal tolerance of a food or beverage product comprising a sweet, low-digestible carbohydrate, wherein the method comprises incorporating D-glucose and beta-glucan and/or polydextrose into the food or beverage product.

In an embodiment, there is provided the use of D-glucose and protein in a method for improving the gastrointestinal tolerance of a food or beverage product comprising a sweet, low-digestible carbohydrate, wherein the method comprises incorporating D-glucose and protein into the food or beverage product.

In an embodiment, there is provided the use of fiber and protein in a method for improving the gastrointestinal tolerance of a food or beverage product comprising a sweet, low-digestible carbohydrate, wherein the method comprises incorporating fiber and protein into the food or beverage product. In a preferred embodiment, there is provided the use of protein and beta-glucan and/or polydextrose in a method for improving the gastrointestinal tolerance of a food or beverage product comprising a sweet, low-digestible carbohydrate, wherein the method comprises incorporating protein and beta-glucan and/or polydextrose into the food or beverage product.

In an embodiment, there is provided the use of D-glucose, fiber and protein in a method for improving the gastrointestinal tolerance of a food or beverage product comprising a sweet, low-digestible carbohydrate, wherein the method comprises incorporating D-glucose, fiber and protein into the food or beverage product. In a preferred embodiment, there is provided the use of D-glucose, protein and beta-glucan and/or polydextrose in a method for improving the gastrointestinal tolerance of a food or beverage product comprising a sweet, low-digestible carbohydrate, wherein the method comprises incorporating D-glucose, protein and beta-glucan and/or polydextrose into the food or beverage product.

According to another aspect of the present invention, there is provided the use of a composition comprising one or more of D-glucose, fiber (e.g. one or more of beta-glucan and polydextrose) and protein in a method for improving the gastrointestinal tolerance of a food or beverage product comprising a sweet, low-digestible carbohydrate.

In an embodiment, there is provided the use of a composition comprising one or more of beta-glucan and polydextrose in a method for improving the gastrointestinal tolerance of a food or beverage product comprising a sweet, low-digestible carbohydrate, wherein the method comprises incorporating one or more of beta-glucan and polydextrose into the food or beverage product.

The composition may be incorporated into the food or beverage product during manufacture. Alternatively, the composition may be incorporated into the food or beverage product following manufacture. The composition may be formulated in any form suitable for including in food or beverage products. For example, the composition may be formulated as a syrup, in powder form, as granules, or in a solution.

In an embodiment, the composition comprises D-glucose. The composition may comprise D-glucose in the absence of fiber and protein. The composition may comprise D-glucose in the absence of beta-glucan, polydextrose and protein.

In another embodiment, the composition comprises fiber. The composition may comprise fiber in the absence of D-glucose and protein. The fiber may be beta-glucan, meaning that, in certain embodiments, the composition may comprise beta-glucan in the absence of D-glucose, protein and other fibers (such as polydextrose). Alternatively, the fiber may be polydextrose, meaning that, in certain embodiments, the composition may comprise polydextrose in the absence of D-glucose, protein and other fibers (such as beta-glucan).

In another embodiment, the composition comprises protein. The composition may comprise protein in the absence of D-glucose and fiber. The composition may comprise protein in the absence of D-glucose, beta-glucan and polydextrose.

In a further embodiment, the composition comprises D-glucose and fiber. The composition may comprise D-glucose and fiber in the absence of protein. The composition may comprise D-glucose and beta-glucan in the absence of other fibers and protein. The composition may comprise D-glucose and polydextrose in the absence of other fibers and protein. The composition may comprise D-glucose, beta-glucan and polydextrose in the absence of other fibers and protein.

In a further embodiment, the composition comprises D-glucose and protein. The composition may comprise D-glucose and protein in the absence of fiber.

In a further embodiment, the composition comprises fiber and protein. The composition may comprise fiber and protein in the absence of D-glucose. The composition may comprise beta-glucan and protein in the absence of other fibers and D-glucose. The composition may comprise polydextrose and protein in the absence of other fibers and D-glucose. The composition may comprise beta-glucan, polydextrose and protein in the absence of other fibers and D-glucose.

The composition may comprise D-glucose, fiber and protein. The composition may comprise D-glucose, beta-glucan and protein in the absence of other fibers. The composition may comprise D-glucose, polydextrose and protein in the absence of other fibers. The composition may comprise D-glucose, beta-glucan, polydextrose and protein in the absence of other fibers.

The composition may comprise D-glucose and beta-glucan, wherein the weight ratio of D-glucose to beta-glucan is between about 5:1 to about 20:1.

Alternatively, the composition may comprise D-glucose and polydextrose, wherein the weight ratio of D-glucose to polydextrose is between about 1:20 to about 20:1 (e.g. about 2:1 to about 20:1).

Further, the composition may comprise beta-glucan and polydextrose, wherein the weight ratio of polydextrose to beta-glucan is between about 5:1 to about 20:1.

In another embodiment, the composition comprises D-glucose, beta-glucan and polydextrose.

When the composition comprises D-glucose, it may be incorporated into a food or beverage product containing a sweet, low-digestible carbohydrate such that the weight ratio of sweet, low-digestible carbohydrate to D-glucose in the food or beverage product is from about 0.5:1 to about 10:1, for example, from about 1:1 to about 5:1, about 1:1 to about 4:1, about 1:1 to about 3:1, or about 1:1.

When the composition comprises beta-glucan, it may be incorporated into a food or beverage product containing a sweet, low-digestible carbohydrate such that the final amount of beta-glucan in the food or beverage product is between about 0.5 g to about 6 g per labeled serving. Also, when the composition comprises beta-glucan, it may be incorporated into a food or beverage product containing a sweet, low-digestible carbohydrate such that the weight ratio of sweet, low-digestible carbohydrate to beta-glucan in the food or beverage product is from about 100:1 to about 5:1, for example, from about 50:1 to about 5:1, about 50:1 to about 10:1, about 40:1 to about 10:1, about 30:1 to about 20:1, or about 25:1.

When the composition comprises polydextrose, it may be incorporated into a food or beverage product containing a low-digestible carbohydrate such that the final amount of polydextrose in the food or beverage product is between about 0.1 g to about 40 g per labeled serving.

According to another aspect of the present invention, there is provided the use of D-glucose for increasing the gastrointestinal tolerance of a food or beverage product comprising a sweet, low-digestible carbohydrate.

According to another aspect of the present invention, there is provided the use of fiber for increasing the gastrointestinal tolerance of a food or beverage product comprising a sweet, low-digestible carbohydrate.

In an embodiment, there is provided the use of beta-glucan for increasing the gastrointestinal tolerance of a food or beverage product comprising a sweet, low-digestible carbohydrate.

In another embodiment, there is provided the use of polydextrose for increasing the gastrointestinal tolerance of a food or beverage product comprising a sweet, low-digestible carbohydrate.

In a further embodiment, there is provided the use of a combination of polydextrose and beta-glucan for increasing the gastrointestinal tolerance of a food or beverage product comprising a sweet, low-digestible carbohydrate.

According to another aspect of the present invention, there is provided the use of protein for increasing the gastrointestinal tolerance of a food or beverage product comprising a sweet, low-digestible carbohydrate.

According to another aspect, there is provided the use of a combination of D-glucose and fiber for increasing the gastrointestinal tolerance of a food or beverage product comprising a sweet, low-digestible carbohydrate.

In an embodiment, there is provided the use of a combination of D-glucose and polydextrose for increasing the gastrointestinal tolerance of a food or beverage product comprising a sweet, low-digestible carbohydrate.

In another embodiment, there is provided the use of a combination of D-glucose and beta-glucan for increasing the gastrointestinal tolerance of a food or beverage product comprising a sweet, low-digestible carbohydrate.

In a further embodiment, there is provided the use of a combination of D-glucose, beta-glucan and polydextrose for increasing the gastrointestinal tolerance of a food or beverage product comprising a sweet, low-digestible carbohydrate.

According to another aspect, there is provided the use of a combination of D-glucose and protein for increasing the gastrointestinal tolerance of a food or beverage product comprising a sweet, low-digestible carbohydrate.

According to another aspect, there is provided the use of a combination of fiber and protein for increasing the gastrointestinal tolerance of a food or beverage product comprising a sweet, low-digestible carbohydrate.

In an embodiment, there is provided the use of a combination of protein and polydextrose for increasing the gastrointestinal tolerance of a food or beverage product comprising a sweet, low-digestible carbohydrate.

In another embodiment, there is provided the use of a combination of protein and beta-glucan for increasing the gastrointestinal tolerance of a food or beverage product comprising a sweet, low-digestible carbohydrate.

In a further embodiment, there is provided the use of a combination of protein, beta-glucan and polydextrose for increasing the gastrointestinal tolerance of a food or beverage product comprising a sweet, low-digestible carbohydrate.

According to another aspect, there is provided the use of a combination of D-glucose, fiber and protein for increasing the gastrointestinal tolerance of a food or beverage product comprising a sweet, low-digestible carbohydrate.

In an embodiment, there is provided the use of a combination of D-glucose, polydextrose and protein for increasing the gastrointestinal tolerance of a food or beverage product comprising a sweet, low-digestible carbohydrate.

In another embodiment, there is provided the use of a combination of D-glucose, beta-glucan and protein for increasing the gastrointestinal tolerance of a food or beverage product comprising a sweet, low-digestible carbohydrate.

In a further embodiment, there is provided the use of a combination of D-glucose, beta-glucan, polydextrose and protein for increasing the gastrointestinal tolerance of a food or beverage product comprising a sweet, low-digestible carbohydrate.

According to a further aspect of the present invention, there is provided one or more of D-glucose, fiber and protein, or a composition comprising one or more of D-glucose, fiber and protein, for use in a method for improving the gastrointestinal tolerance of food and beverage products comprising a sweet, low-digestible carbohydrate in accordance with (earlier aspects of the invention.

In an embodiment, there is provided one or more of D-glucose, beta-glucan, polydextrose, and protein, or a composition comprising one or more of D-glucose, beta-glucan, polydextrose and protein, for use in a method for improving the gastrointestinal tolerance of food and beverage products comprising a sweet, low-digestible carbohydrate in accordance with earlier aspects of the invention.

According to another aspect of the present invention, there is provided a food or beverage product comprising a sweet, low-digestible carbohydrate and one or more of D-glucose, fiber and protein, wherein the one or more of D-glucose, fiber and protein are present in an amount effective to improve the gastrointestinal tolerance of said food or beverage product. The D-glucose, fiber (which includes one or more of beta-glucan and polydextrose) and protein may be present in the food or beverage product in the amounts already described herein.

EXAMPLES

The invention will now be illustrated by means of the following examples, it being understood that these are intended to explain the invention, and in no way to limit its scope.

Example 1

Study on the Gastrointestinal Tolerance of D-Allulose

A dose escalation study was conducted in a total of 24 pre-screened subjects. 18 subjects were treated with 6 subjects acting as the control. D-allulose was presented in a flavored beverage and the beverages were consumed with a food at breakfast and lunch so that the total daily dose was divided in half at each serving (FIG. 1). The control beverage contained 25 g of sucrose per serving.

The beverages were served with breakfast (slice of cheese and lean pocket) and lunch (hot pocket) consumed 4 hrs apart. Acute treatment protocols were performed with at least a 3 day washout period between, escalating the daily dose amount at each visit until what was considered a maximum tolerated dose was achieved. Subjective gastrointestinal GI symptoms were assessed on a scale of 0-3 (0=no symptoms, 1=mild symptoms, 2=moderate symptoms, 3=severe symptoms). The six symptoms assessed were: 1) abdominal distension, 2) abdominal pains, 3) borborygmus, 4) increased flatus, 5) loose stools, and 6) nausea-vomiting. The GI symptoms were assessed at times 0, 2, 4 and 24 hours relative to the breakfast meal.

The doses of allulose tested were 30 g/d; 50 g/d; 70 g/d×2 (i.e. repeated once); 60 g/d (de-escalation). Of the 18 test subjects, 11 were men and 7 were women. The median age of all subjects was 48.5 y/o with an age range of 28-78.

Figure 2:
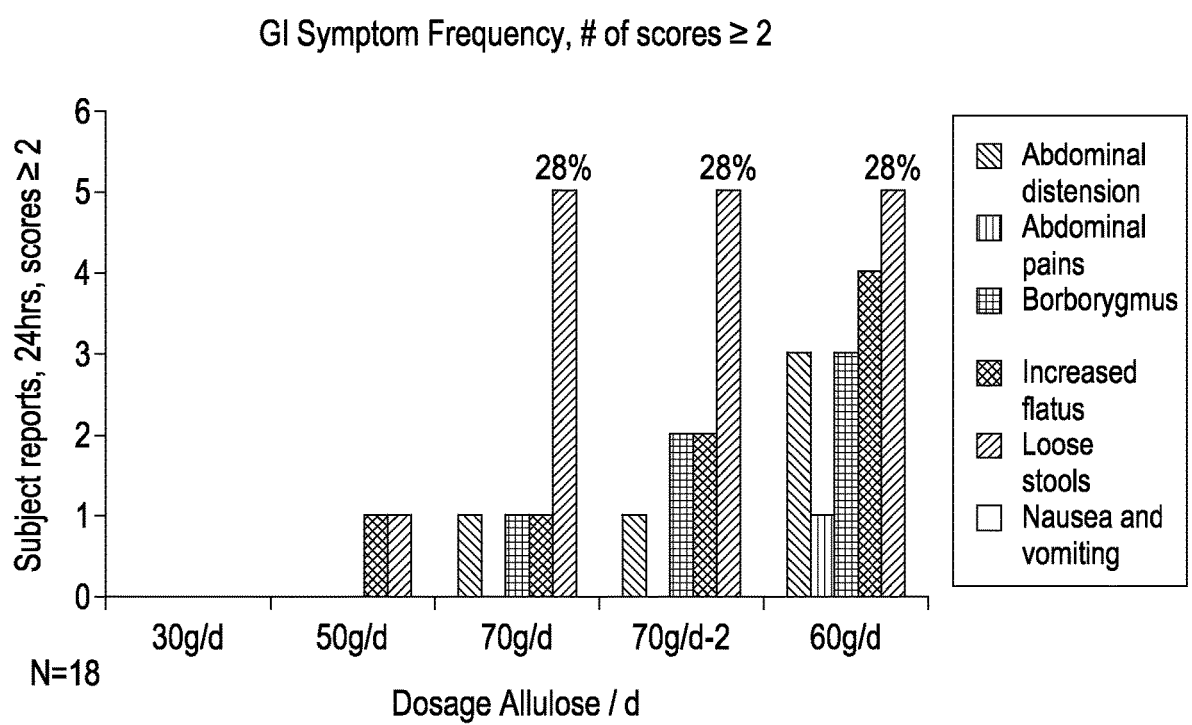
FIG. 2 shows the results of the dose escalation study of Example 1. Each bar on the chart corresponds to a specific gastrointestinal symptom for a particular dosage. The height of the bars corresponds to the number of subjects who reported a subjective gastrointestinal symptom score of 2 or 3 at a given dose.

In the study, 28% of subjects experienced loose stools at doses of 60 g/d and 70 g/d (FIG. 2). Additionally gas and bloating were also prevalent accompanying symptoms.

Example 2

Study on Gastrointestinal Tolerance—D-Allulose Plus Glucose

Figure 3:
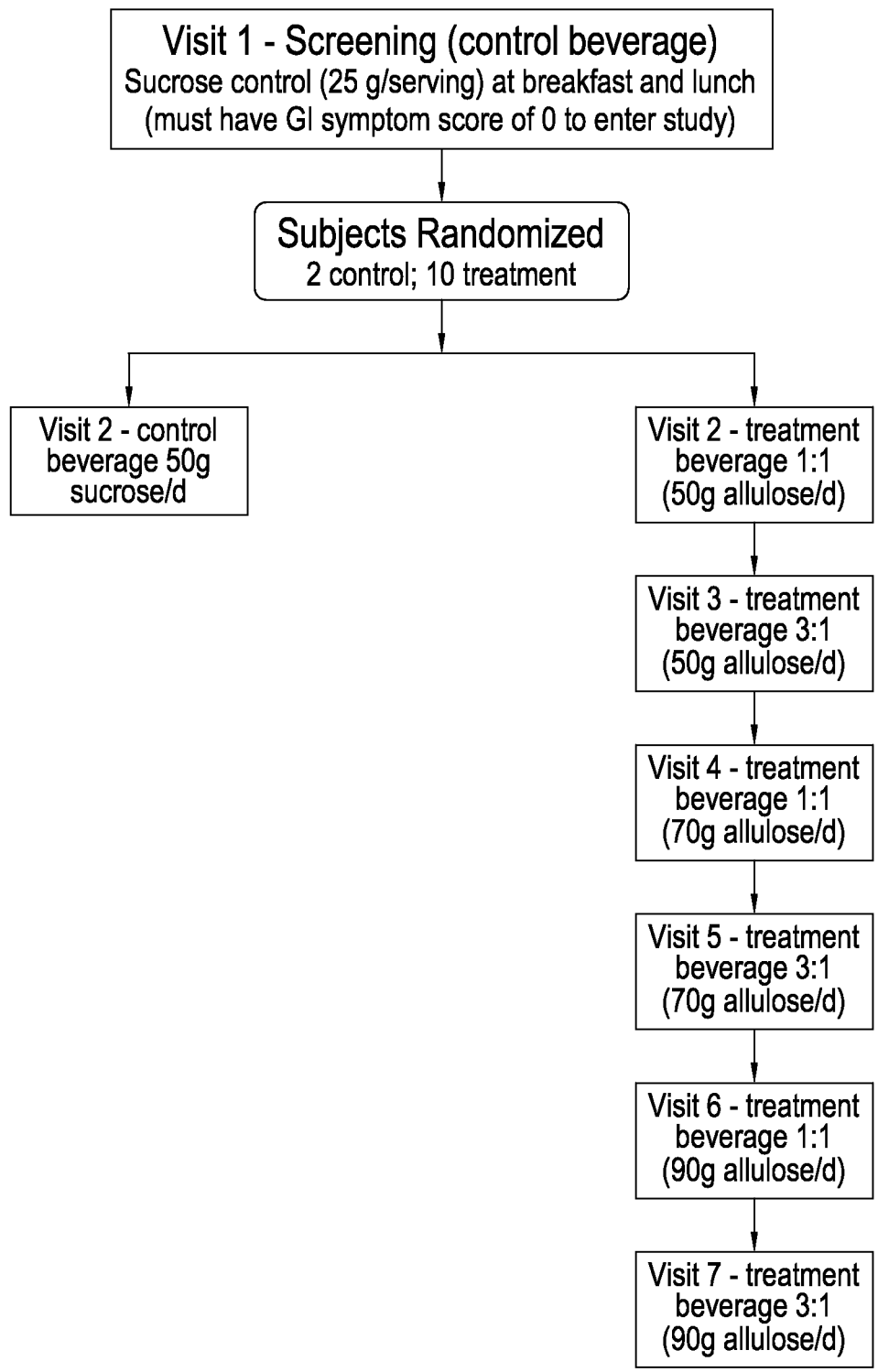
FIG. 3 is a schematic of the treatment protocol used in Example 2.

A dose escalation study was conducted in 10 test subjects and compared to 2 control subjects. D-allulose was presented with D-glucose in a flavored beverage either at equal amounts (1:1) or at an amount of 1:3 (D-glucose:D-allulose) following the same protocol design as the study in Example 1 (see Table 1 and FIG. 3).

TABLE 1

Doses of D-allulose and D-glucose provided in the study

| Beverage | D-Allulose dose Grams/day | D-Allulose dose Grams/serving | D-Glucose dose Grams/serving | D-Glucose/ D-allulose ratio |
| --- | --- | --- | --- | --- |
| Control | 0 (control) | 0 | 0 (25 g sucrose) | n/a |
| Bev 1 | 50 | 25 | 25 | 1:1 |
| Bev 2 | 50 | 25 | 8.35 | 1:3 |
| Bev 3 | 70 | 35 | 35 | 1:1 |
| Bev 4 | 70 | 35 | 11.65 | 1:3 |
| Bev 5 | 90 | 45 | 15 | 1:1 |
| Bev 6 | 90 | 45 | 45 | 1:3 |

Figure 4:
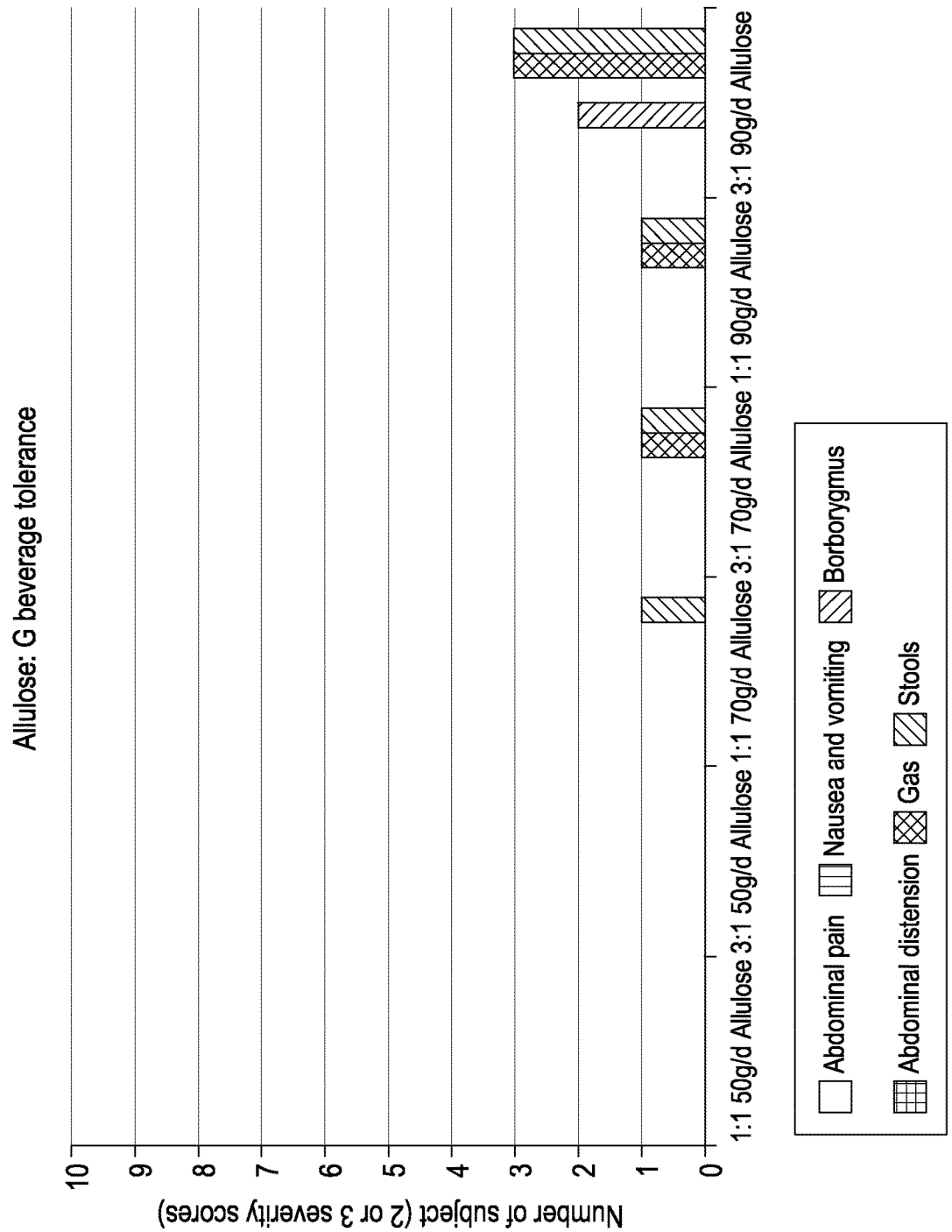
FIG. 4 shows the results of the tolerance study of Example 2. Each bar on the chart corresponds to a specific gastrointestinal symptom for a particular dosage. The height of the bars corresponds to the number of subjects who reported a subjective gastrointestinal symptom score of 2 or 3 at a given dose.

The beverages were consumed with a meal at breakfast and lunch time. As shown in FIG. 4, at 90 g of D-Allulose per day (divided into two 45 g/serving doses), a 1:1 mixture of D-glucose to D-allulose in a beverage appeared superior, with 20% fewer subjects with recorded tolerance findings –1 subject with loose stool at 1:1 vs. 3 subjects with loose stool when the dose was 3:1. The addition of D-glucose reduced loose stool occurrences compared to the first study such that, at the 70 g D-allulose/d dose, only 10% of subjects experienced loose stools (c.f. 28% in the study of Example 1).

In conclusion, the results show that the composition of foods or beverages to include D-glucose positively affects the gastrointestinal tolerance of low-digestible carbohydrates by reducing gastrointestinal symptoms of bloating, gas and diarrhea.

Example 3

Study on Gastrointestinal Tolerance

Overview

In this Example, subjects tested 4 different beverages, consumed in the morning with at least one week washout between test days. The beverages were consumed on an empty stomach, and there was instruction for subjects to wait 2 hours before having any other food. The primary outcome was the total gastrointestinal symptom scores over 24-hours for loose stool GI symptom derived from a GI symptoms rating diary.

The 4 test beverages (8 oz./236.6 ml) were flavoured with a strawberry mix and contained: 1) 25 g of D-allulose; 2) 25 g of D-allulose and 25 g of D-glucose; 3) 25 g of D-allulose and 1 g of beta-glucan fiber; or 4) 25 g of sucrose.

Methods

Ten volunteers were instructed with the following information on how to consume the test beverages, monitor gastrointestinal symptoms and 24 hour stool observations using a Bristol Stool Form:

The day before the test drink, avoid consumption of foods which are known to cause you GI distress or gas (see below).

Fast for 10-14 hours overnight prior to consumption of the test drink.

Do not consume other foods for 2 hours after treatment beverage (water only).

Record all bowel movements using a Bristol Stool Scale diary (Bristol Stool Form).

At 2, 4 and 24 hours post consumption of the treatment beverage, provide the symptom scorning for each of 6 gastrointestinal tolerance questions (see below).

The subjects were provided with the following examples of gas-producing foods and beverages to avoid: beans (legumes; not "green beans") and food items, such as chili, hummus, lentil soup, bean soup, etc; vegetables such as broccoli, cauliflower, cabbage, brussel sprouts, onions, mushrooms, artichokes, and asparagus; fruits, such as pears, apples, and peaches; whole grains such as whole wheat and bran; sodas, fruit drinks (especially apple juice and pear juice), and other drinks that contain high-fructose corn syrup; sugar-free candies and foods that contain sugar alcohols, such as xylitol, mannitol, and sorbitol; and foods with supplemental fibers such as, Fiber One® cereals and bars.

The subjects were also advised to avoid any other foods that may cause them GI distress or gas during the study day and also the evening before.

On the day of the test, the subjects followed the below set of instructions:
1. Testing start times begin when you start consuming the drink; record date and time you begin on the diary.
2. Consume the test drink at the same time each week.
   a. Consume the entire drink 8 oz. (236.6 ml) drink in under 15 minutes.
   b. Refill the drink container with water and consume as a chaser.
   c. You may have additional water after 60 minutes as desired.
3. Record GI symptom scores at 2, 4 and 24-hours after starting drink consumption.
4. You may eat a snack or breakfast 2 hours after the test drink.
5. Record all bowel movements and the Bristol Stool type during the 24-hour observation period.
6. Resume normal food consumption for the day; however avoid foods which you know may cause gastric upset or gas for the 24-hour observation period.

The symptom scoring for the 6 gastrointestinal GI tolerance questions was assessed by the subjects on the basis of the following 4-point scales: 1) Abdominal pains (0 (i.e. none)=no or transient pain; 1 (i.e. mild)=occasional aches and pains interfering with some social activities; 2 (i.e. moderate)=prolonged and troublesome aches and pains causing requests for relief and interfering with many social activities; and 3 (i.e. severe)=severe or crippling pains with impact on all social activities); 2) Nausea and vomiting (0=no nausea; 1=occasional episodes of short duration; 2=frequent and prolonged nausea but no vomiting; and 3=continuous nausea with frequent vomiting); 3) Borborygmus (0=no or transient borborygmus; 1=occasional troublesome borborygmus of short duration; 2=frequent and prolonged episodes which can be mastered by moving without impairing social performance; and 3=continuous borborygmus severely interfering with social performance); 4) Abdominal distention (0=no or transient distention; 1=occasional discomfort of short duration; 2=frequent and prolonged episodes which can be mastered by adjusting the clothing; and 3=continuous discomfort seriously interfering with social performance); 5) Increased flatus (0=no increased flatus; 1=occasional discomfort of short duration; 2=frequent and prolonged episodes interfering with some social activities; and 3=frequent episodes seriously interfering with social performance); and 6) Loose stools (0=normal consistency; 1=somewhat loose; 2=runny; and 3=watery).

Results

Figure 5:
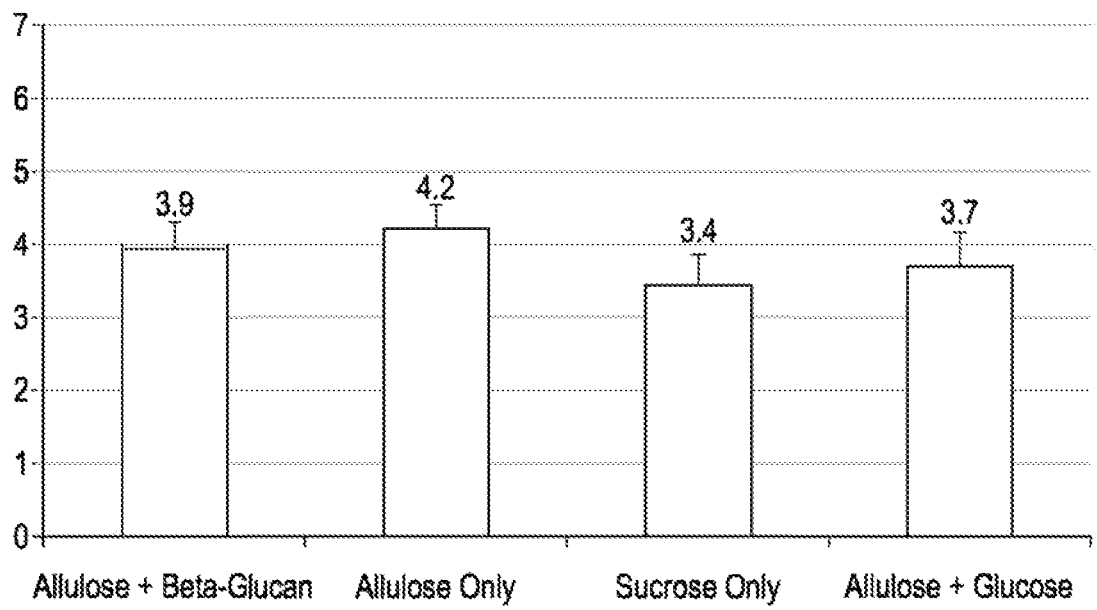
FIG. 5 shows the Bristol Stool Test score averages for the study of Example 3. Each bar on the chart corresponds to the average Bristol Stool score in relation to each beverage tested. The height of the bars corresponds to the average score (out of 7).
Figure 6:
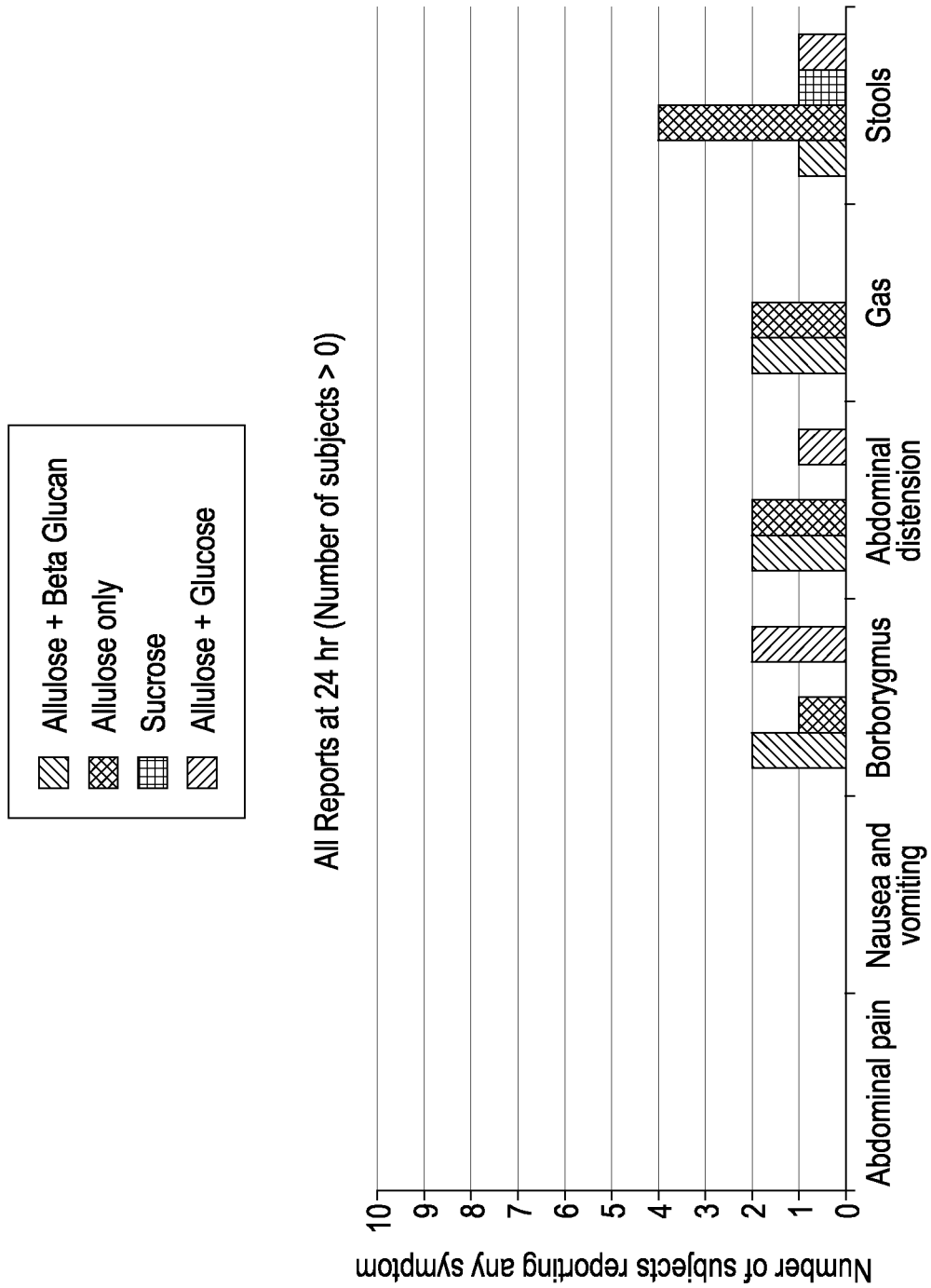
FIG. 6 shows the results of the gastrointestinal (GI) tolerance study of Example 3. The height of the bars corresponds to the number of subjects who reported any symptom score at 24 hours post consumption.

The Bristol Stool test scores were scored from 1-7. Each subject's scores were averaged for the 24 hour observation period then averaged per treatment group. The results are presented in FIG. 5. The GI symptom scores relating to the 6 GI tolerance questions are presented in FIG. 6.

There was a softening effect with the allulose treatment compared to the sucrose treatment (negative control). Improvements were seen when beta-glucan and D-glucose were added to the beverage. Softer stools were found in the following order: allulose>allulose+beta-glucan>allulose+D-glucose>sucrose.

The number of people reporting symptoms was greatest in the allulose only group. Both D-glucose and beta-glucan decreased reports of symptoms compared to allulose only beverage overall. There was an observable decrease in symptoms in the 2 and 4 hour questions when D-glucose or beta-glucan was added to the beverages compared to allulose alone (results not shown).

In conclusion, improvements were seen with beta-glucan and D-glucose. Softer stools were found in the following order: allulose>allulose+beta-glucan>allulose+D-glucose>sucrose. D-Glucose addition to the beverage also decreased recordings of gas, abdominal distention and loose stools, compared to allulose alone. Beta-glucan addition to the beverage also decreased loose stool symptoms. This data demonstrates that, when either D-glucose or oat beta-glucan fiber are consumed together with allulose in a beverage, there is a decrease in symptoms created by an acute large dose of allulose.

The invention claimed is:

1. A method for improving the gastrointestinal tolerance of a food or beverage product comprising D-allulose consumed by a human subject in need thereof, wherein the method comprises incorporating one or more of D-glucose, fiber or protein into the food or beverage product and whereby one or more symptoms selected from the group consisting of abdominal distention, abdominal pains, borborygmus, increased flatus, loose stools, and nausea/vomiting are reduced in occurrence and severity when the food or beverage product is consumed by the human subject.

2. The method according to claim 1, wherein the method comprises incorporating a fiber into the food or beverage product and the fiber is one or more of a beta-glucan or polydextrose.

3. The method according to claim 1, wherein the method comprises incorporating D-glucose into the food or beverage product.

4. The method according to claim 3, wherein the method further comprises incorporating a beta-glucan into the food or beverage product.

5. The method according to claim 4, wherein the method further comprises incorporating polydextrose into the food or beverage product.

6. The method according to claim 3, wherein the method further comprises incorporating polydextrose into the food or beverage product.

7. The method according to claim 3, wherein the D-allulose is present in the food or beverage product in a weight ratio to D-glucose of from about 0.5:1 to about 10:1.

8. The method according to claim 7, wherein the D-allulose is present in the food or beverage product in a weight ratio to D-glucose of from about 1:1 to about 3:1.

9. The method according to claim 1, wherein the method comprises incorporating fiber into the food or beverage product.

10. The method according to claim 1, wherein the method comprises incorporating beta-glucan into the food or beverage product.

11. The method according to claim 10, wherein the method further comprises incorporating polydextrose into the food or beverage product.

12. The method according to claim 10, wherein the beta-glucan is oat beta-glucan.

13. The method according to claim 10, wherein the beta-glucan is in the form of a fraction rich in soluble dietary fibers containing at least about 20% and up to about 40% beta-glucan (on a dry weight basis) of mean molecular weight of at least about 800 kDa.

14. The method according to claim 13, wherein the beta-glucan is in the form of a fraction rich in soluble dietary fibers containing about 35% beta-glucan (on a dry weight basis) of mean molecular weight of at least about 800 kDa.

15. The method according to claim 10, wherein the beta-glucan is present in an amount between about 0.5 g and about 6 g per labeled serving of the food or beverage product.

16. The method according to claim 10, wherein the beta-glucan is present in an amount of about 0.01% by weight to about 20% by weight with respect to the total weight of the food or beverage product.

17. The method according to claim 1, wherein the method comprises incorporating polydextrose into the food or beverage product.

18. The method according to claim 17, wherein the polydextrose is present in an amount of about 0.1% by weight about 80% by weight with respect to the total weight of the food or beverage product.

19. The method according to claim 17, wherein the polydextrose is present in an amount of about 0.1 g to about 40 g per labeled serving of the food or beverage product.

20. The method according to claim 1, wherein the method comprises incorporating protein into the food or beverage product.

21. The method according to claim 20, wherein the method further comprises incorporating one or more of D-glucose or fiber into the food or beverage product.

22. The method according to claim 1, wherein the protein is present in an amount of about 0.1 g to about 40 g per labeled serving of the food or beverage product.

23. The method according to claim 1, wherein the protein is present in an amount of about 0.1% by weight to about 80% by weight with respect to the total weight of the food or beverage product.

24. The method according to claim 1, wherein the D-allulose is present in the food or beverage product in a total amount from about 1 g to about 100 g per labeled serving.

25. A food or beverage product comprising D-allulose and one or more of D-glucose, fiber or protein, wherein the one or more of D-glucose, fiber or protein are present in an amount effective to improve the gastrointestinal tolerance of said food or beverage product whereby one or more symptoms selected from the group consisting of abdominal distension, abdominal pains, borborygmus, increased flatus, loose stools, and nausea/vomiting are reduced in occurrence and severity when the food or beverage product is consumed by a human subject in need thereof.

* * * * *